US00PP09813P

United States Patent [19]

Stemkens

[11] Patent Number: Plant 9,813

[45] Date of Patent: Feb. 25, 1997

[54] GERMANIUM PLANT NAMED 'SANWHITE'

[75] Inventor: Henricus G. W. Stemkens, Hoorn, Netherlands

[73] Assignee: S&G Seeds B.V., Enkhuizen, Netherlands

[21] Appl. No.: 571,308

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 9,373 11/1995 Schumann ..... Plt./87.12

P.P. 9,522 4/1996 Schumann et al. ..... Plt./87.12

*Primary Examiner*—Howard J. Locker

*Attorney, Agent, or Firm*—Lynn Marcus-Wyner

[57] ABSTRACT

A new ivy-leaved geranium particularly distinguished by its well-branched shape and compact growth, early appearing blush white single flowers which do not set seed with good precocity and floral richness.

1 Drawing Sheet

BACKGROUND OF THE NEW PLANT

The present invention comprises a new distinct cultivar of ivy-leaved geranium, botanically known as *Pelargonium peltatum* hybrid. The new cultivar is propagated from cuttings resulting from the cross of G53 and I229. G53 is a blush white flowering peltatum having no pollen. G53 is not commercially available and is not known by any synonyms. I229 is also a white colored peltatum, with vigorous growth and having pollen. I229 is not commercially available and is not known by any synonyms. Neither G53 nor I229 have been patented. As a result of this cross the present cultivar was created in 1990 in Enkhuizen, Netherlands and has been repeatedly asexually reproduced by cuttings in Enkhuizen, Netherlands and Stuttgart, Germany over a four year period. It has been found to retain its distinctive characteristics through successive propagations, and this novelty appears to be firmly fixed.

DESCRIPTION OF THE DRAWING

This new geranium plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new geranium. The data which defines these characteristics were collected from asexual reproductions carried out in Enkhuizen, Netherlands. The plant history was taken on 12 week old plants, blossomed under natural light in a greenhouse. Color readings were taken in the greenhouse under ambient light. Color references are primarily to The R.H.S. Colour Chart of The Royal Horticulture Society of London.

THE PLANT

Classification:

*Botanical.*—*Pelargonium peltatum* — Hybrid.

*Commercial.*—Ivy-leaved geranium.

Parentage:

*Female parent.*—A seedling named G53 is one of our seedlings from our G-generation of plants bred in 1982.

*Pollen parent.*—A seedling named I229 is one of our seedlings from I-generation of plants bred in 1984.

Form: Very compact, hanging.

Shape: Round.

Stalk length: About 160–210 mm in April and 400–480 mm in September.

Number of stems per stalk: Approximately 6–8 from May until the end of September.

Number of stalks per plant: Approximately 8–10 in October.

Internode length: About 35–65 mm depending on the light where the plant is propagated.

Growth rate: Hanging and vigorous.

Strength: Very good.

Branching character: Very good branching.

Foliage:

*Quantity.*—Many robust leaves.

*Size.*—Small, from 45–53 1 mm.

*Shape.*—5 lobed, peltate.

*Texture.*—Smooth, hairy at young leaf stage (1 cm long), becoming smoother with increased maturity.

*Zonation.*—Almost circular 2 mm, very light brown.

Ribs and veins: 5 Ribs.

Color:

*Upper side.*—Medium green 141A.

*Lower side.*—Light green 137C.

Length of leaf stem: 25–35 mm.

THE BUD

Peduncle length: 90–125 mm, depending on the season.

Size:

*Diameter.*—2–3 mm.

*Length.*—10 mm.

Shape: Elliptical.

Form: Ovoid and pointed.

Rate of opening: Medium.

Color:

*When sepals first divide.*—137C.

*When petals begin to unfurl.*—138A.

Sepals:

*Color.*—Inside — 138B. Outside — 138A.

*Form.*—Standing up.

Pedicel:

*Length.*—About 22–28 mm.

*Strength.*—Very strong, the florets are arranged asymmetric around the middle of the cluster. The florets are approximately 30 mm in diameter.

*Color.*—138A.

THE FLOWER

Blooming habit: Continuous and profusely from April until October.

Size: Approximately 50–60 mm.
Borne: In a cluster having between 4–8 flowers per cluster.
Form: Horizontal symmetric, quite open. When the flowers mature, the petals curl back.
Petals:
*Numbers.*—5 per floret, between 100–120 clusters in one season per plant.
*Arrangement.*—2 upper petals, longer and broader. 3 lower petals, smaller.
*Form.*—Obcordate.
*Color.*—Outer petal — 65C, very light pink. Inside petal — White (lower) or red purple (upper).
*Markings.*—See pattern.
*Reverse side.*—White with pink nerves color 56B.
*Pattern.*—The upper two petals have two long red-purple margins (color 59C) which fade into the veins. Between the two lines thereis a small pink blotch. The reverse side has the same stripes, but lighter in color. The lower petals have very small (2mm) pink lines, mostly 2. The outer parts of the petals are very light pink colored.
*Texture.*—Smooth.
*Appearance.*—Satiny. Petals remain on stem about 5–7 days depending on the weather.
Persistence: Petals drop, so no picking of matured clusters.
Disease resistance: Sanwhite does not suffer from Botrytis.
Weather resistance: Sanwhite is not unusually affected by wet or hot weather.
Lasting quality:
*On the living plant in pot.*—about 10–14 days.
*As a cut flower.*—About 5 days.
Fragrance: No perceptible fragrance.

REPRODUCTIVE ORGANS

Stamens:
*Anthers.*—Totally shriveled, and yellow in color.
*Filaments.*—Usually 7, about 1 mm in length, and white in color.
Pollen: None.
Pistils:
*Number.*—One.
*Length.*—Approximately 6 mm.
*Stigmas.*—Pink in color, divided in 5 papillae.
Ovaries: Green in color.
Seed: Non-fertile.

What is claimed:

1. A new and distinct cultivar of ivy-leaved geranium plant substantially as herein shown and described, particularly distinguished by its very short internodes and well branched plant, and its early appearing blush white single flowers that do not set seed.

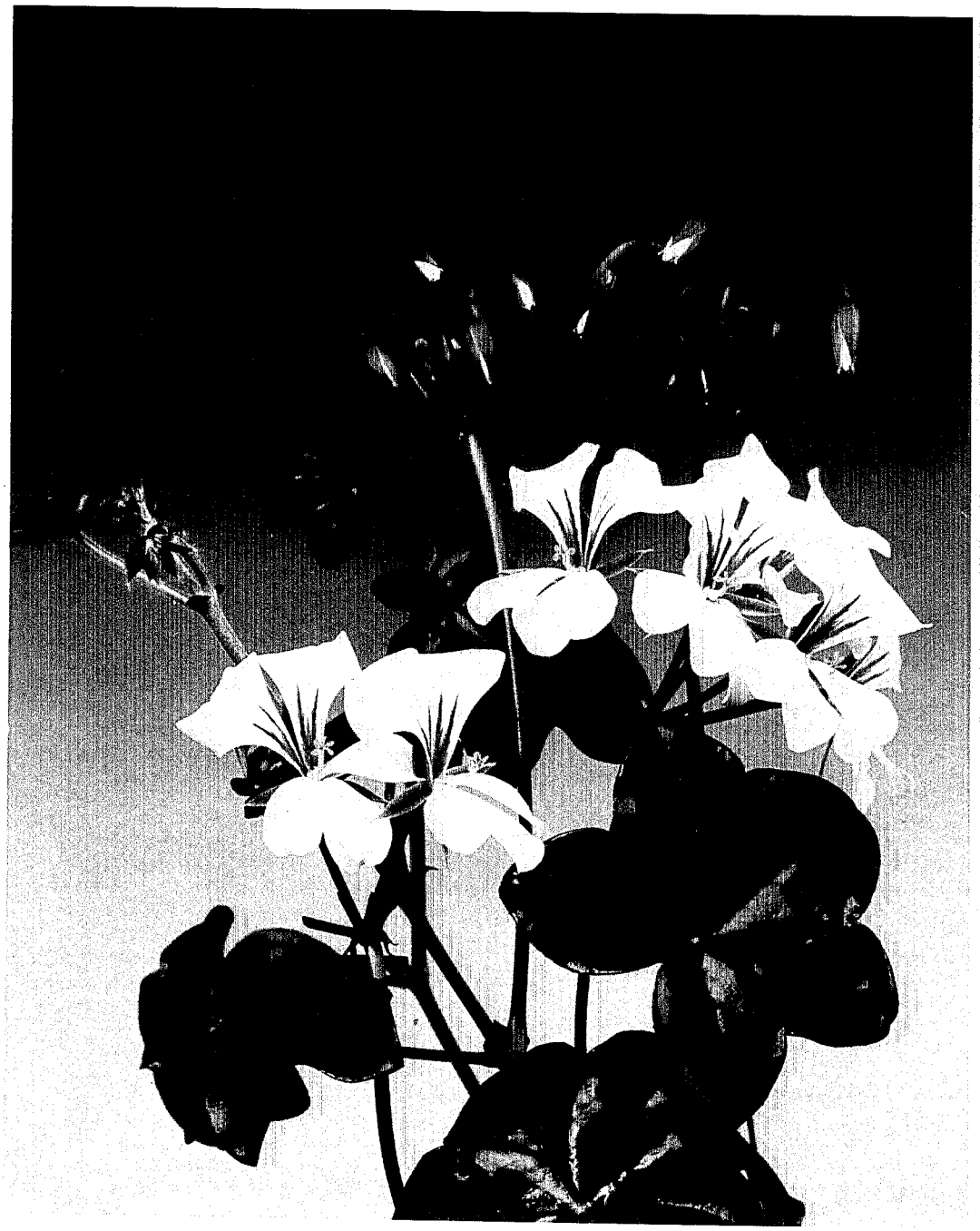

* * * * *